(12) United States Patent
Salomir et al.

(10) Patent No.: US 8,740,801 B2
(45) Date of Patent: Jun. 3, 2014

(54) RF SHIELD FOR AN ULTRASOUND TRANSDUCER FOR USE IN A MAGNETIC RESONANCE SYSTEM

(75) Inventors: Rares Salomir, Evires (FR); Magalie Viallon, Lyons (FR)

(73) Assignee: Siemens Aktiengesellschaft, Munich (DE)

( * ) Notice: Subject to any disclaimer, the term of this patent is extended or adjusted under 35 U.S.C. 154(b) by 581 days.

(21) Appl. No.: 12/916,731

(22) Filed: Nov. 1, 2010

(65) Prior Publication Data

US 2012/0108976 A1     May 3, 2012

(51) Int. Cl.
*A61B 8/00*     (2006.01)

(52) U.S. Cl.
USPC ............................................... 600/459

(58) Field of Classification Search
USPC .................... 600/459, 411, 412, 422
See application file for complete search history.

(56) References Cited

U.S. PATENT DOCUMENTS

| | | | |
|---|---|---|---|
| 6,776,758 B2 * | 8/2004 | Peszynski et al. | 600/437 |
| 7,314,447 B2 * | 1/2008 | Park et al. | 600/459 |
| 7,798,969 B2 * | 9/2010 | Hirayama et al. | 600/459 |

* cited by examiner

*Primary Examiner* — Long V. Le
*Assistant Examiner* — Lawrence Laryea
(74) *Attorney, Agent, or Firm* — Schiff Hardin LLP

(57) ABSTRACT

An ultrasound transducer for use in a magnetic resonance system is provided with an RF shield formed of electrically conductive material and having an interior cavity configured to receive the ultrasound transducer therein. The RF shield substantially precludes coupling between the ultrasound transducer, and any coupling medium that is employed, and the transmission and reception coils of the magnetic resonance system.

5 Claims, 2 Drawing Sheets

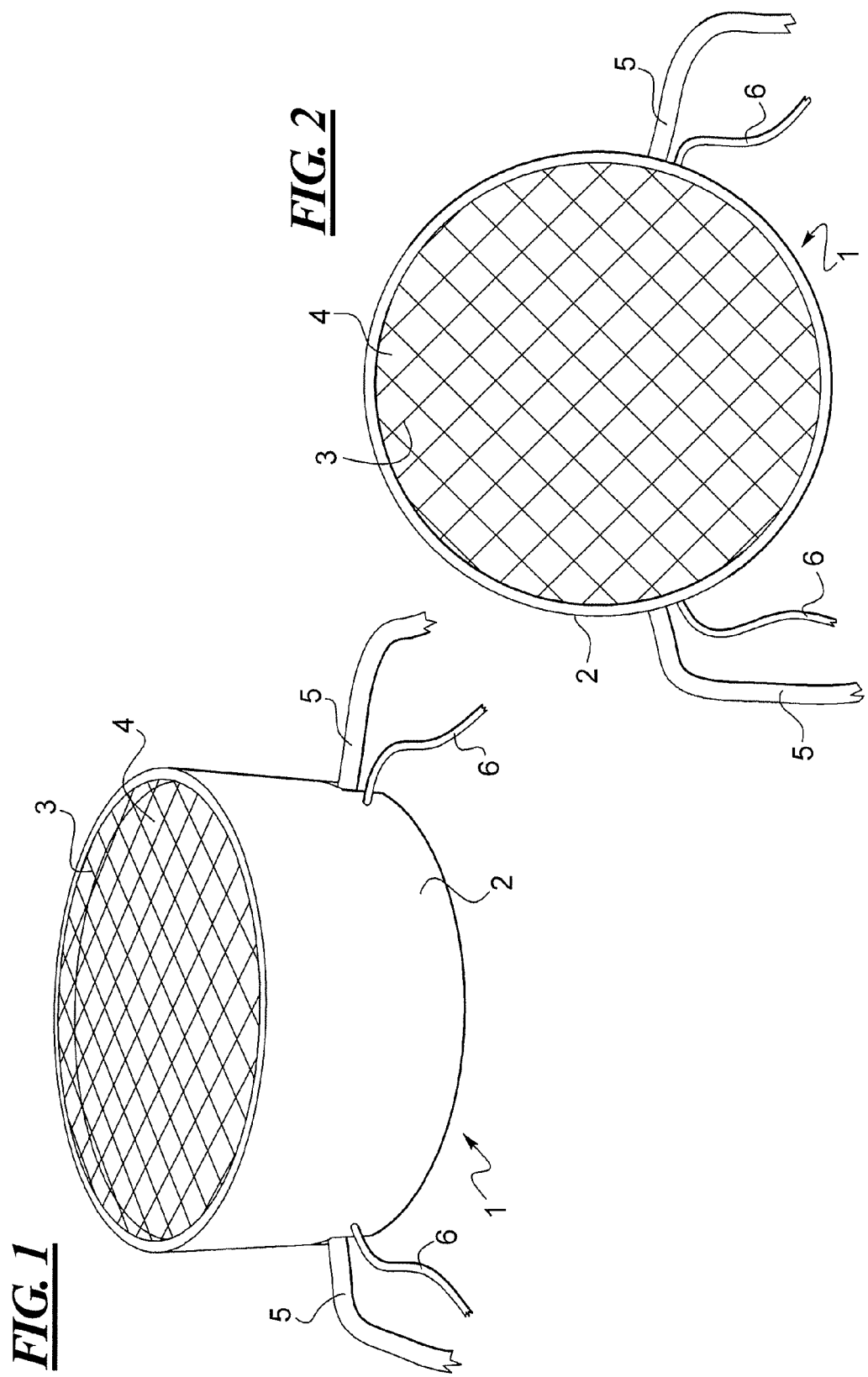

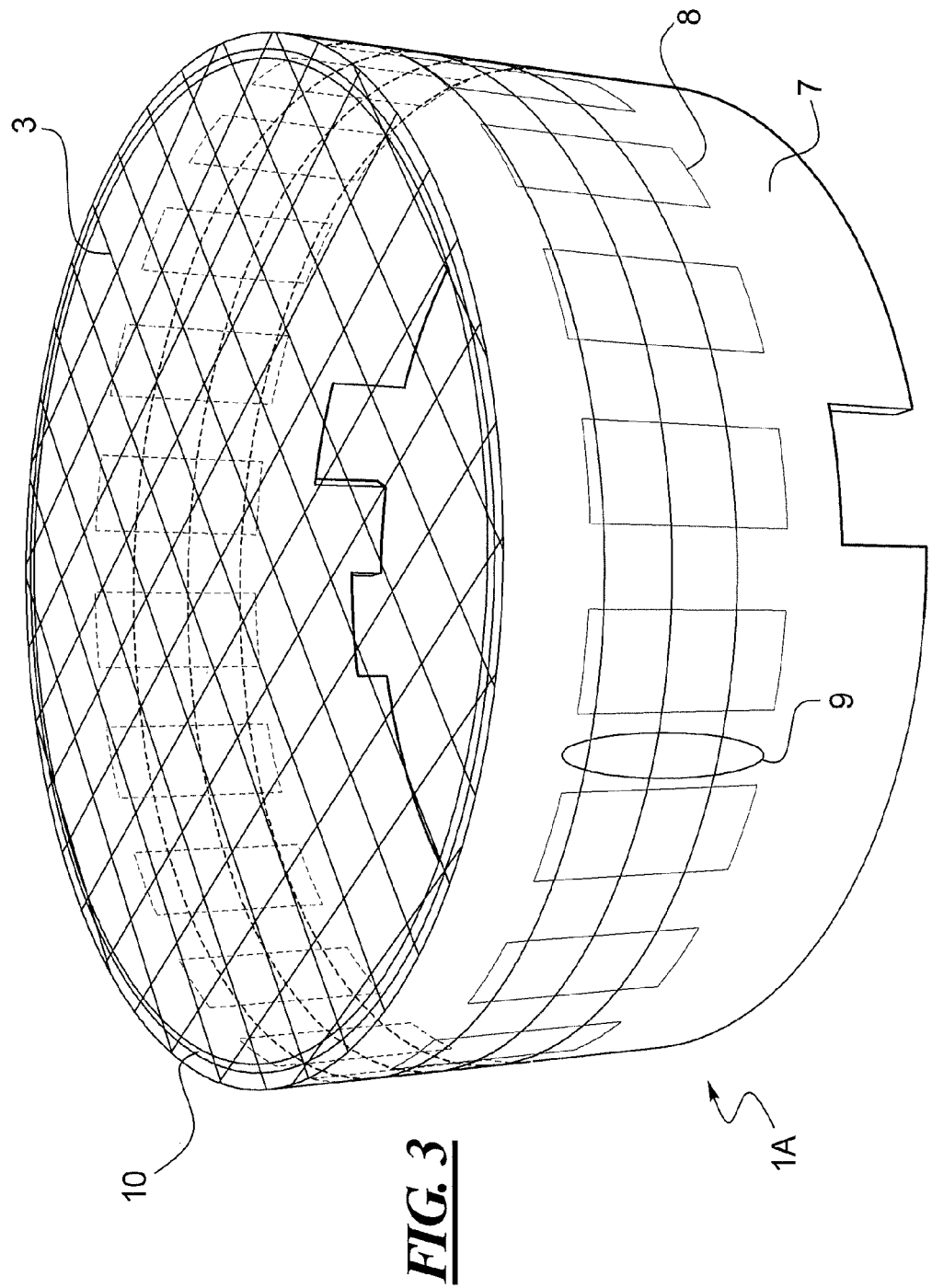

RF SHIELD FOR AN ULTRASOUND TRANSDUCER FOR USE IN A MAGNETIC RESONANCE SYSTEM

BACKGROUND OF THE INVENTION

1. Field of the Invention

The present invention concerns a radio-frequency (RF) shield for an ultrasound transducer, or the type used in a magnetic resonance imaging or spectroscopy system.

2. Description of the Prior Art

When operating an ultrasound system such as a HIFU system, the ultrasound energy (ultrasound waves) must be transferred from the ultrasound transducer to the target body, such as a patient, via a suitable medium. It may also be advantageous for the medium to be a liquid that is capable of transporting heat away from the transducer or the body surface. Typically degassed water is used as such a medium.

Several problems can occur when operating such an ultrasound device in conjunction with a magnetic resonance imaging or spectroscopy system, as is the case in a magnetic resonance guided HIFU (MRg HIFU) procedure.

One problem is that RF antennas that are used for transmission in the magnetic resonance system may couple to the liquid or to the transducer itself. Such coupling may damage the ultrasound transducer, due to the high RF transmission powers that are used in magnetic resonance. Additionally, there will likely be energy (power) absorbed by the liquid or by the transducer, so that the RF transmission power for the magnetic resonance system has to be correspondingly increased. Moreover, the presence of the transducer and the liquid may cause the magnetic resonance transmission coil to become detuned, resulting in reflections toward the amplifier that is connected to the coil, and again requiring a higher transmission power. Lastly, the dielectric effect of the medium may adversely reduce the field homogeneity of the RF transmission field, thereby causing artifacts in the resulting image. In magnetic resonance systems that employ very high fields, this dielectric effect may cause specific absorption great hot spots, thereby causing discomfort, or even injury, to the patient.

Another category of problems results from the radio-frequency antennas of the magnetic resonance system that are used for reception coupling to the liquid or the transducer itself. This coupling of the reception antenna, due to losses in the liquid or in the transducer, may cause the magnetic resonance reception coil to detect (receive) a higher level of thermal noise. Moreover, the reception coil may become detuned, resulting in a higher noise factor in the amplifier connected to the reception coil, and thus a reduced sensitivity to the useful magnetic resonance signal that is being simultaneously detected.

Additionally, the electrical RF ultrasound signal that is sent to the ultrasound transducer (composed of one or more fundamental frequencies, their harmonics, and other frequencies that may exist in an "unclean" signal) may couple into the reception coil, and any portion of this coupled-in signal that is then digitized in the processing of the received MR signal will cause artifacts in the reconstructed image. The ultrasound signal may also possibly cause switching of diodes connected to the coil from the intended blocking state to a conducting state, thereby turning the coil off (precluding reception), or possibly causing the amplifier to saturate.

Another category of problems is due to the fact that the coupling medium may itself produce a magnetic resonance signal. It may be unavoidable for the field of view of the magnetic resonance system to be chosen so as to include a signal produced by the coupling medium, in order to avoid signal "fold-in," and this may in turn increase the scanning time, or may reduce the achievable image resolution. Moreover, if the medium exhibits a flow, this may cause an artifact in the reconstructed magnetic resonance images.

Examples of such ultrasound systems are HIFU systems, non-focused therapeutic ultrasound lithotripsy, diagnostic ultrasound, ultrasound arrangements that induce shear waves for magnetic resonance-based shear-wave elastography, and other comparable ultrasound systems.

A number of techniques are known that address some of the problems noted above, but no technique is known that alleviates all of the above-cited problems.

Coupling media are known that do not produce contrast in a magnetic resonance image, such as oil, perfluorocarbon, etc. Assuming the medium that is employed does, in fact, not produce MR contrast, this approach may limit fold-in artifacts and flow artifacts. Such media, however, may still exhibit electrical loss and dielectric properties, which will define whether and how strongly the transmission and reception coils will couple to the medium. The use of such non-contrast-producing media, however, does not address the problem of coupling of the transmission coil to the ultrasound transducer, itself, and coupling between the ultrasound transducer to the magnetic resonance reception coil. Other factors that must be considered when choosing alternative liquids are cost, heat-carrying properties, ultrasound properties, aging properties, bio-compatibility and compatibility with other materials of the device.

Signal suppression techniques are also known, such as saturation bands and flow suppression, which reduce the signal originating from the ultrasound coupling medium. Such techniques, however, have not proven to sufficiently suppress the signal, and moreover have an impact on the signal acquisition. Moreover, because saturation bands are executed with a large flip angle, this further increases the local specific absorption ratio.

An ultrasound transducer has a ground plane, and therefore another known technique to alleviate coupling between the ultrasound transducer and the transmission and reception antennas is to segment the ground plane of the transducer. Such segmentation, however, is not always sufficient.

To alleviate the coupling between the electrical RF ultrasound signal and the reception coil, it is known to use blocking circuits that filter out unwanted signal contributions. Such blocking circuits are integrated into the reception coils, or their signal chain. This approach, therefore, requires the use of a specialized coil, and cannot be used in systems that are already fitted with conventional coils.

A further approach has been to synchronize the ultrasound sonication (activation) times so that magnetic resonance signal reception and ultrasound sonication do not occur simultaneously. This requires a synchronization circuit and architecture, and may limit the duty cycle of the ultrasound and/or of the magnetic resonance imaging. In the case of HIFU, for example, the available duty cycle is already significantly reduced when HIFU activation is interleaved with multi-slice magnetic resonance data acquisition. Using sequential acquisition of multiple slices enables a higher duty cycle of HIFU, but with the penalty of a lower signal-to-noise ratio in the magnetic resonance signal, and a lower temporal resolution.

SUMMARY OF THE INVENTION

In accordance with the present invention, RF shielding is provided for the ultrasound transducer and the coupling medium. The RF shielding is formed by an electrically conducting enclosure that has an open interior that is of a size and shape to encompass the particular type of ultrasound transducer that is employed, as well as at least a small region around the transducer at which "exposed" coupling medium might be present. The shield has leads connected thereto allowing the shield to be placed at a suitable electrical potential.

The open top of the shield housing is covered with an electrically conducting wire mesh that is electrically connected to shield housing. The bottom of the shield remains open in order to receive the ultrasound transducer.

By RF shielding the transducer and the coupling medium, the problems noted above can be mitigated. The RF energy transmitted into the shield cavity is substantially reduced, so coupling from the magnetic resonance body coil to the ultrasound medium and to the transducer is correspondingly reduced. Conversely, radio-frequency energy is prevented from exiting from the interior of the shield cavity. Therefore, coupling to the magnetic resonance reception coil is also minimized. Moreover, the magnetic resonance signal originating from inside the shield cavity is reduced both by reducing the amount of signal excited by the transmission field and that received by the reception coil.

Because the shield is open at its top side, except for the aforementioned wire mesh, it is largely transparent to ultrasound transmission.

BRIEF DESCRIPTION OF THE DRAWINGS

FIG. 1 is a perspective of an embodiment of an RF shield for an ultrasound transducer constructed in accordance with the present invention.

FIG. 2 is a plan view of the RF shield of FIG. 1.

FIG. 3 is a perspective view of a further embodiment of an RF shield in accordance with the present invention.

DESCRIPTION OF THE PREFERRED EMBODIMENTS

An RF shield 1 in accordance with the present invention is shown in FIGS. 1 and 2. The RF shield 1 has, in this embodiment, a generally cylindrical shield body 2 composed of electrically conductive material, such as copper, that has an interior cavity having a size and shape allowing an ultrasound transducer 4 to be placed therein. The interior cavity of the shield body 2 may also be large enough to encompass a small annular area around the transducer 4 at which "exposed" coupling medium may be located. The otherwise open top of the shield body 2 is covered by a wire mesh 3, that is also composed of electrically conductive material, and that is electrically connected to the shield body 2.

The shield body 2 has openings therein that allow cables 5 to proceed thereto for supplying power to the ultrasound transducer in the interior cavity.

The shield 1 is provided with its own electrical leads 6 that allow the entirety of the shield body and the wire mesh 3 to be placed at a selected electrical potential.

Certain types of ultrasound transducers may be provided with a cooling system, in which water or some other coolant circulates beneath the ultrasound transducer. When the transducer and the RF shield 1 are used in the magnetic resonance system, the RF shield 1 blocks the magnetic resonance signal originating from the coolant (water) from producing flow artifacts in the resulting magnetic resonance image.

The basic physical principle on which the RF shield 1 is based is that the electromagnetic flux induces electrical currents in the shield, which are rapidly attenuated because of the electrical coupling with the wire in the environment of the RF shield 1. The shield converts the electromagnetic incident energy into heat in the surrounding water. If there are free electrical charges (ions) in the surrounding water, the energy dissipation is faster. Even with the use of demineralized water, however, the water molecules are still highly polar, and are oscillating with the local electrical field so as to dissipate the energy in a sufficiently effective manner by dielectric coupling.

Because of this basic principle, the RF shield 1 cannot function solely in air, nor completely immersed in a non-polar insulator medium, such as oil.

Although shown as a hollow cylinder in the embodiment of FIGS. 1 and 2 (and in the embodiment of FIG. 3 as well), the shield body 2 can be of any suitable shape, yet only be necessary that the size and shape of the interior cavity thereof are configured to receive and contain the type of ultrasound transducer that is being shielded.

The further embodiment of an RF shield 1A is shown in FIG. 3. In this embodiment, the shield body 7 has a number of windows 8 therein so that the area inside the cavity of the shield 7 can still be made at least somewhat visible in the resulting magnetic resonance image, without significantly detracting from the shielding effect. Electrically conducting wires 9 can be provided around the circumference of the shield body 7, over the windows 8.

In this embodiment, since the material forming the shield body 7 is relatively thin, the presence of the windows 8 may reduce the mechanical stability of the overall shield, and thus a plastic insert 10 may be provided that surrounds the inner periphery of the shield body 7.

In each of the embodiments, in order to avoid eddy currents from the switched gradients that are used in magnetic resonance imaging, the RF shield can be segmented.

The wires of the mesh 3 preferably have an individual thickness that is less than or equal to approximately 10% of the wavelength of the ultrasound waves that are used. As an alternative to the use of wire mesh 3, a thin electrically conductive foil may be used, which similarly does not significantly attenuate the ultrasound radiation. Such a foil has the advantage of providing a sealing of the interior cavity.

The cables 5 that lead to the ultrasound transducer 4 should themselves be individually shielded.

Although modifications and changes may be suggested by those skilled in the art, it is the intention of the inventors to embody within the patent warranted hereon all changes and modifications as reasonably and properly come within the scope of their contribution to the art.

We claim as our invention:

1. A shielded ultrasound transducer system comprising:
   an ultrasound transducer that emits ultrasound;
   a shield body comprising of electrically conductive material and having an open interior cavity having a size and a shape that receives said ultrasound transducer therein, said cavity having an opening therein proceeding from an interior to an exterior of said cavity;
   a substantially ultrasound-transparent covering formed by an electrically conductive wire mesh extending over said opening of said shield body, through which said ultrasound emitted by said ultrasound transducer proceeds; and
   said shield body and said covering being electrically connected with each other to form RF shielding that includes said covering and that RF shields said internal cavity, including said opening.

2. A shielded ultrasound transducer system as claimed in claim 1 wherein said shield body is a hollow cylinder.

3. A shielded ultrasound transducer system as claimed in claim 1 wherein said shield body comprises a plurality of circumferential openings therein.

4. A shielded ultrasound transducer system as claimed in claim 1 comprising electrically conductive wires circumferentially extending around said shield body over said openings.

5. A shielded ultrasound transducer system as claimed in claim 1 comprising a plastic insert in said interior cavity adjacent to an interior periphery of said shield body.

* * * * *